US011260172B2

(12) United States Patent
Barmaimon et al.

(10) Patent No.: US 11,260,172 B2
(45) Date of Patent: Mar. 1, 2022

(54) ANGLED INTEGRATED SOFT CANNULA

(71) Applicant: FLEX LTD., Singapore (SG)

(72) Inventors: Eyal Barmaimon, Haifa (IL); Lior Shtram, Tel-Aviv (IL); Shai Finkman, Haifa (IL); Erez Levy, Atlith (IL); Nadav Cohen, Haifa (IL)

(73) Assignee: FLEX LTD., Singapore (SG)

( * ) Notice: Subject to any disclaimer, the term of this patent is extended or adjusted under 35 U.S.C. 154(b) by 19 days.

(21) Appl. No.: 16/295,799

(22) Filed: Mar. 7, 2019

(65) Prior Publication Data

US 2019/0275237 A1      Sep. 12, 2019

Related U.S. Application Data

(60) Provisional application No. 62/640,436, filed on Mar. 8, 2018.

(51) Int. Cl.
*A61B 17/34*    (2006.01)
*A61M 5/142*    (2006.01)
(Continued)

(52) U.S. Cl.
CPC ........ *A61M 5/158* (2013.01); *A61M 5/14248* (2013.01); *A61B 17/3431* (2013.01);
(Continued)

(58) Field of Classification Search
CPC ........... A61B 17/3439; A61B 17/3431; A61M 5/158; A61M 5/14248; A61M 2005/14252; A61M 2005/1581; A61M 2005/1583; A61M 2005/1585; A61M 25/01; A61M 25/06; A61M 25/065; A61M 2205/0216;
(Continued)

(56) References Cited

U.S. PATENT DOCUMENTS 5,281,218 A    1/1994    Imran
6,878,136 B2   4/2005    Fleury et al.
(Continued)

OTHER PUBLICATIONS

International Search Report and Written Opinion dated Jul. 2, 2019 issued in corresponding international patent application No. PCT/IB2019/051907.

(Continued)

*Primary Examiner* — Shefali D Patel
*Assistant Examiner* — Avery Smale
(74) *Attorney, Agent, or Firm* — Volpe Koenig

(57) ABSTRACT

A device and a method for insertion of a cannula into a user's tissue are disclosed. A patch pump comprising a non-linear needle path with a first bend may be provided. A rigid needle may be located in the non-linear needle path and may be composed of a material that allows the rigid needle to maintain a bend at the first bend when traversing the non-linear needle path. A movement mechanism may be configured to apply a first force on a first end of the rigid needle to cause the rigid needle to traverse the non-linear needle path from a first needle position to a second needle position. The cannula may receive a second force from a second end of the rigid needle when the movement mechanism applies the first force on the first end of the rigid needle and may be configured to traverse from a first cannula position to a second cannula position based on the second force.

19 Claims, 7 Drawing Sheets

(51) Int. Cl.
*A61M 5/158* (2006.01)
*A61M 5/172* (2006.01)

(52) U.S. Cl.
CPC ....... *A61B 17/3439* (2013.01); *A61B 17/3462* (2013.01); *A61M 5/1723* (2013.01); *A61M 2005/14252* (2013.01); *A61M 2005/1581* (2013.01); *A61M 2005/1583* (2013.01); *A61M 2005/1585* (2013.01)

(58) Field of Classification Search
CPC .............. A61M 5/142; A61M 5/14244; A61M 2005/14256; A61M 2005/1426; A61M 2005/1586; A61M 2025/0004; A61M 2025/0175; A61M 2025/0266; A61M 25/0606; A61M 25/0631

See application file for complete search history.

(56) References Cited

U.S. PATENT DOCUMENTS

| 2002/0123740 | A1 | 9/2002 | Flaherty et al. |
| 2006/0142698 | A1* | 6/2006 | Ethelfeld ............. A61B 5/6848 604/157 |
| 2009/0048563 | A1* | 2/2009 | Ethelfeld ............. A61M 5/158 604/174 |
| 2015/0196719 | A1 | 7/2015 | Uchiyama |
| 2016/0361013 | A1 | 12/2016 | Schmid |
| 2017/0043133 | A1* | 2/2017 | Amano ............ A61M 25/0606 |
| 2017/0119959 | A1 | 5/2017 | Cole et al. |

OTHER PUBLICATIONS

International Search Report and Written Opinion dated Jul. 10, 2019 issued in corresponding international patent application No. PCT/IB2019/051908.
Non-Final Office Action dated Jul. 12, 2021 in corresponding U.S. Appl. No. 16/295,811.

* cited by examiner

ANGLED INTEGRATED SOFT CANNULA

This application claims the benefit of U.S. Provisional Application No. 62/640,436 having a filing date of Mar. 8, 2018, which is incorporated by reference as if fully set forth.

BACKGROUND

There is a strong market need for an apparatus that can enable the subcutaneous self-administration of solutions such as medication in a wearable format factor. For instance, the treatment of diabetes requires the subcutaneous delivery of insulin. As a result, wearable pumps that deliver a medication to a patient may be used to administer such solutions. These pumps may incorporate the medication, pumping mechanism, and infusion set into a patch that attaches to a patient's skin, thus eliminating the need for external systems.

Patients may wear patch pumps for a prolonged period of time and, accordingly, patient comfort and ease of use is a consideration in the design and manufacturing of such patch pumps.

SUMMARY

A device and method for cannula insertion into a user's tissue are disclosed herein. A patch pump comprising a non-linear needle path with a bend may be provided. A rigid needle may be located in the needle path and may be composed of a material that allows the rigid needle to maintain a bend at the first bend when traversing the non-linear needle path. A movement mechanism may be configured to apply force on a first end of the rigid needle to cause the rigid needle to traverse the non-linear needle path from a first needle position to a second needle position. A cannula may be configured to receive a force from a second end of the rigid needle when the movement mechanism applies the force on the first end of the rigid needle and configured to traverse from a first cannula position to a second cannula position based on the force.

BRIEF DESCRIPTION OF THE DRAWINGS

A more detailed understanding may be had from the following description, given by way of example in conjunction with the accompanying drawings wherein.

DETAILED DESCRIPTION

Examples of different pumps and needle insertion mechanism implementations will be described more fully hereinafter with reference to the accompanying drawings. These examples are not mutually exclusive, and features found in one example can be combined with features found in one or more other examples to achieve additional implementations. Accordingly, it will be understood that the examples shown in the accompanying drawings are provided for illustrative purposes only and they are not intended to limit the disclosure in any way. Like numbers refer to like elements throughout.

Below are described an apparatus and methods for delivering solutions such as pharmaceutical drugs and/or biologics to a patient. The apparatus and methods may allow for prescription or standard off-the-shelf drug cartridges to be utilized without compromising the sterility of the solution. This may enable a patient to self-administer a solution in a self-contained wearable patch pump form factor that is cost effective and comfortable to wear. The disclosure subject matter provided herein may allow the manufacturing and use of a patch pump that is small enough in size to be comfortable to wear.

Figure 1A:
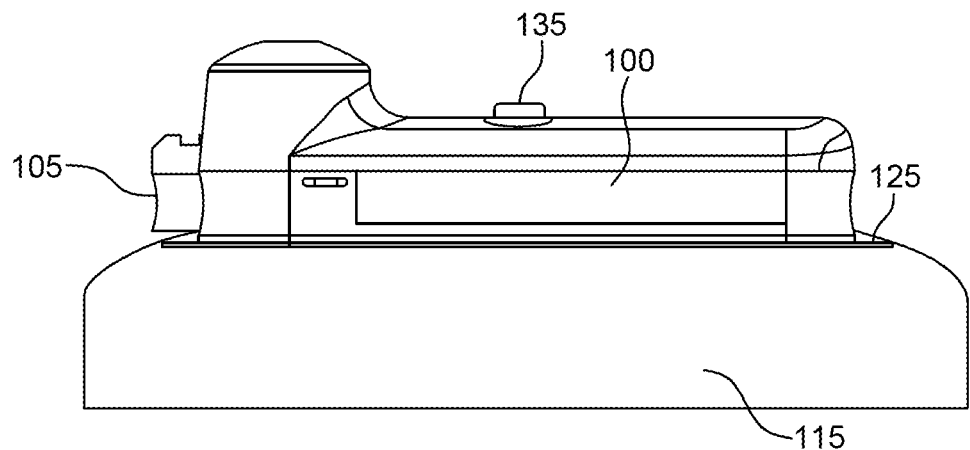
FIG. 1A is a graphic depiction of a patch pump on a user.

FIG. 1A is a graphic depiction of a patch pump 100 on a patient 115. The patch pump 100 includes a base 125 that contacts the patient's skin. In some embodiments, the base 125 includes an adhesive liner that affixes the patch pump 100 to the patient 115. The patch pump 100 may further include a user flow control switch 135. The user flow control switch 135 may enable a user to pause and control the flow rate of a solution. The patch pump 100 further includes a start button 105 that may be pressed by a user to cause a cannula and/or needle to be inserted into the patient and the solution to flow from a drug container 130 through the cannula and/or needle into the patient.

Figure 1B:
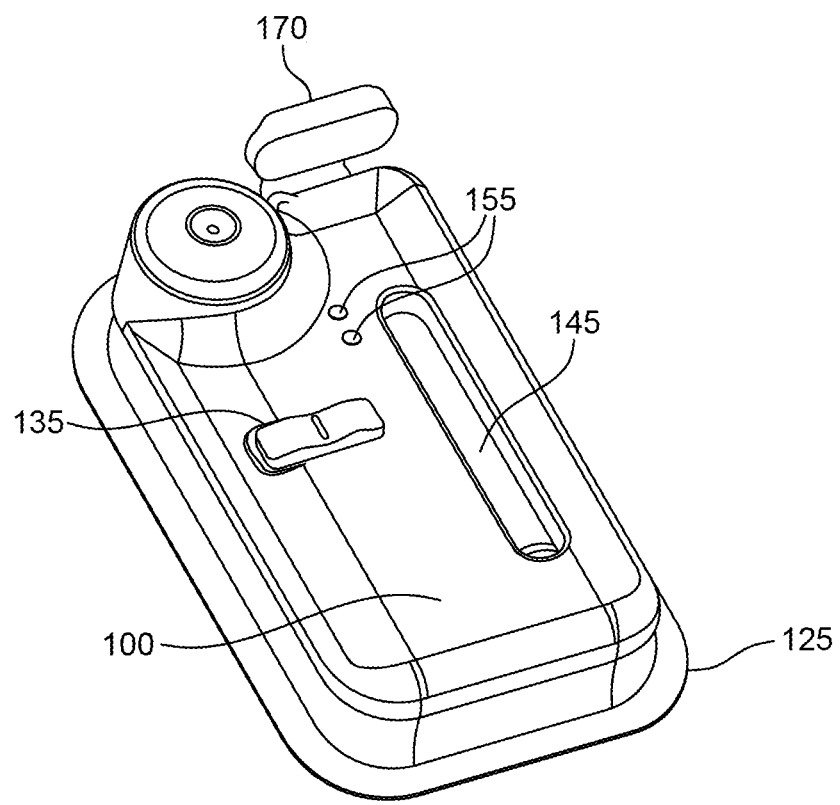
FIG. 1B is a graphic depiction of the outer casing of an embodiment of a patch pump.

As shown in FIG. 1B, the patch pump 100 may further include a drug viewing window 145. This viewing window may enable a user to view the amount of a solution that remains in the drug container 130. The patch pump 100 may also include one or more visual indicators 155. The visual indicators 155 provide feedback on the operational status of the system. The operational status of the system may include warnings such as an over/under temperature warning, drug expiration warning and over/under pressure warning. In addition, the operational status may include information indicating that the drug is being administered, how much time is remaining for the drug dosage to be completed and the current flow rate. The visual indicators may include LEDS, LCD displays or other similar display technologies known in the art. The information that is displayed by visual indicators may also be wirelessly transmitted to a mobile computing device such as a smart phone utilizing any of the wireless communication methods known in the art.

The patch pump 100 may further include a removable safety 170. The removable safety mechanically engages the start button 105 and prohibits the start button 105 from being involuntary pressed.

Figure 1C:
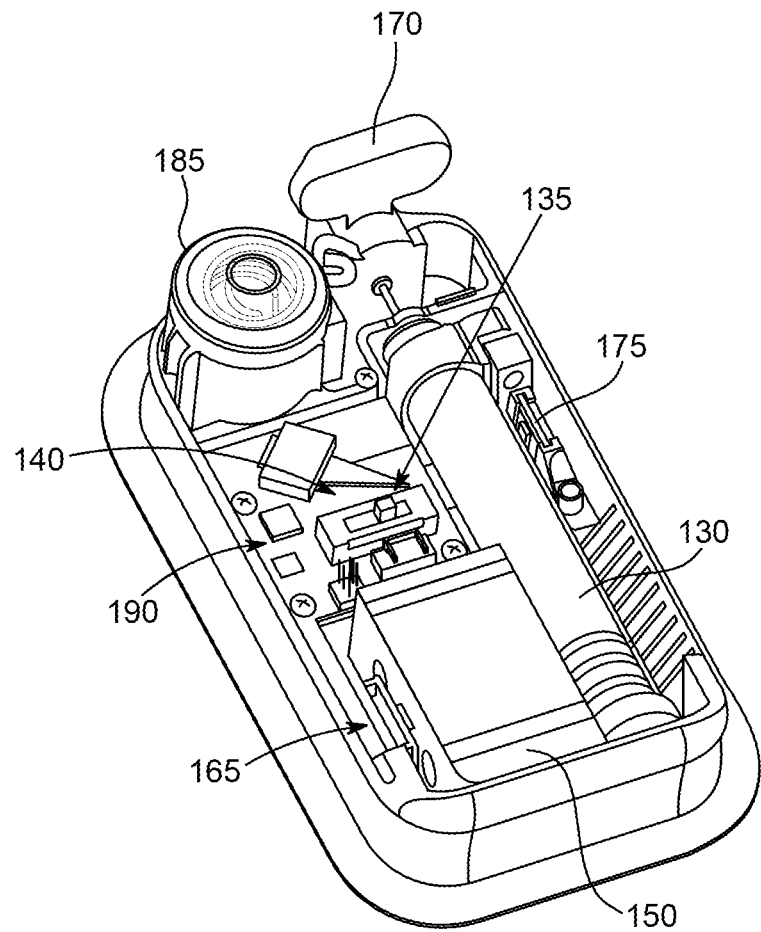
FIG. 1C is a graphic depiction of an embodiment of a patch pump with the outer casing removed.

FIG. 1C shows additional components of a patch pump 100. The patch pump 100 may also include a needle insertion component 185 that is mechanically connected to the start button 105. In addition, the patch pump 100 includes an electronic circuit board 140 that includes control circuitry for the visual indicators 155, user flow control switch 135 and a motion system 150. In addition, the electronic circuit board 140 may be communicatively connected to one or more sensors. These sensors may include pressure sensor 165 and proximity sensor 175 and may include on or more sensors such as a haptic feedback sensor (not shown) or other indicator. The electronic circuit board 140 may also include a memory 190. The memory 190 may store dosing instructions for the administration of the solution. In addition, the memory 190 may also store information regarding the administration of the solution. This information IT may include, time, date, and flow rate when the solution was administered. The electronic circuit board 140 may control the visual indicators 155 and the motion system 150 based on the information stored in the memory and the feedback from the sensors. The electronic circuit board 140 may include a communication module that enables the transmission of information stored in the memory 190 to a wireless computing device. In addition, the communication module may also receive updated dosing instructions that are subsequently stored in the memory 190.

A device, such as a patch pump, configured in accordance with the disclosed subject matter may consume a smaller footprint than traditional patch pumps and/or needle mechanisms. Such a device may be configured to allow the movement of a needle in a first plane and the needle may cause the movement of a cannula in a second plane. As an example, a needle may be pushed from right to left on a horizontal plane and a distal end of the needle may then push a cannula from top to bottom in a vertical plane. The movement in two different planes may allow the device to be smaller than if the movement of the needle and the cannula was in the same plane.

As disclosed herein, such a device may contain a curved needle path and a needle configured to follow the curved path to change the direction of the needle's motion and its corresponding force. The force in the changed direction may cause a cannula, mechanically in contact with the needle, to move in the changed direction.

Figure 2A:
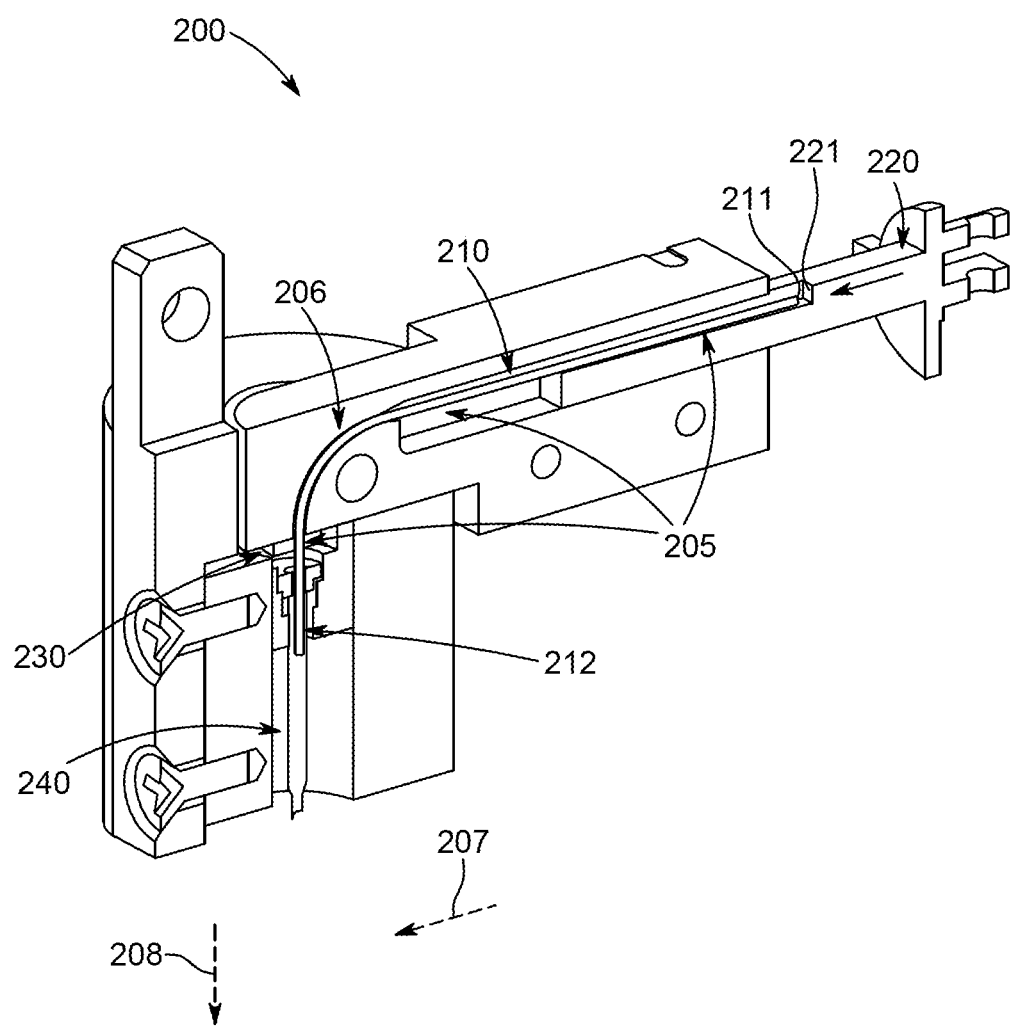
FIG. 2A is a graphical depiction of a needle insertion mechanism at a first position.

FIG. 2A is a graphic depiction of a needle insertion mechanism 200. The needle insertion mechanism 200 may be included in the needle insertion component 185 of patch pump 100, as shown in FIGS. 1A-C or may be part of a different patch pump or other solution delivery mechanism which requires the use of a needle and/or cannula. Accordingly, the needle insertion mechanism 200 may be configured to operate with the components shown in FIGS. 1A-C or, alternatively, may be configured to operate with a subset of the components shown in FIG. 1A-C or none of the components shown in FIGS. 1A-C. Patch pumps with different or modified components then those shown in FIGS. 1A-C may be used with needle insertion mechanism 200.

FIG. 2A shows a cross section of a needle insertion mechanism 200, which includes a needle path 205. As shown, the needle path 205 may be slightly larger than a rigid needle 210 that is contained within the needle path 205. The dimensions of the needle path 205 may be determined based on the size or diameter of the rigid needle 210 such that the needle path 205 is large enough to allow the rigid needle 210 to move along the needle path 205. Additionally, the dimensions of the needle path 205 may be small enough such that when the rigid needle 210 moves along/traverses the needle path 205, it does not experience any unintended movement or shaking within the needle path 205.

The needle path 205 may be non-linear such that it may contain a curve 206 that is part of the needle path 205. It will be understood that although a single curve 206 is described herein, the needle path 205 may contain two or more curves in order to enable a rigid needle 210 to traverse an intended path. The curve 206 may alter a direction of the needle path 205 from a first direction in a first plane to a second direction in a second plane. As shown in FIGS. 2A-D, the needle path 205 may begin in a first substantially horizontal plane in the direction shown by 207. The needle path 205 may change directions at curve 206 to a substantially vertical plane in the direction shown by 208. It will be understood that although a substantially 90 degree change within a Z plane is shown in FIGS. 2A-D, the needle path 205 may alter a direction at any angel and within any plane. As an example, the needle path 205 may alter a direction at a 60-degree angle or, alternatively, the needle path 205 may alter a direction at a 30-degree angle. The specific angle or range of angle that the needle path 205 alters a direction at may be determined based on the application of the needle insertion mechanism 200. For example, a needle insertion mechanism 200 that requires a flatter profile may include a lower angle (e.g., 30 degree angle) whereas a needle insertion mechanism 200 that requires a smaller with may include a higher angle (e.g., 90 degree angle). According to this example, the insertion mechanism 200 with the 30 degree angle may be smaller in height but longer in width than the insertion mechanism 200 with the 90 degree angle.

According to an implementation, a needle insertion mechanism 200 that includes a needle path 205 with a 90-degree change in direction may occupy a smaller footprint in a first dimension than a needle path 205 with a smaller (e.g., 60 degree) change in direction. For example, a needle insertion mechanism 200 with a needle path 205 with a 90-degree change in direction may be shorter in length than a similar needle insertion mechanism 200 with a needle path 205 with a 60-degree change in direction. However, a needle insertion mechanism 200 that includes a needle path 205 with a 90-degree change in direction may occupy a larger footprint in a second dimension than a needle path 205 with a smaller (e.g., 60 degree) change in direction. Continuing the example, the needle insertion mechanism 200 with a needle path 205 with a 90-degree change in direction may be lower in height than a similar needle insertion mechanism 200 with a needle path 205 with a 60-degree change in direction.

A rigid needle 210 may be composed of any applicable material that enables the rigid needle 210 to maintain a bend along a needle path 205. Additionally, a rigid needle 210 may be composed of any applicable material that enables the rigid needle 210 to cause a cannula 240 to be pushed in a desired direction, as further disclosed herein. As non-limiting examples, a rigid needle 210 may be composed of nitinol, stainless steel, or the like.

A rigid needle 210 may be inserted into a needle path 205 during the manufacturing process such as after some of the components of the needle insertion mechanism 200 have been assembled. Alternatively, according to an implementation, a rigid needle 210 may be inserted into a needle path 205 after the needle insertion mechanism 200 has been fully assembled. According to an implementation, a rigid needle 210 may be replaced or removed and reinserted into the needle path 205.

As shown in FIG. 2A, a movement mechanism 220 may move along the needle path 205. As shown, the movement mechanism 220 may move along a portion of the needle path 205 before the curve 206 of the needle path 205 begins. Accordingly, the movement mechanism 220 may move along the needle path 205 in a single plane.

A movement mechanism 220 may move in the direction of the needle path 205 as a result of a force applied to the movement mechanism 220. The force applied to the movement mechanism may be caused by a manual or mechanical movement or, alternatively, may be caused by one or more electronic components. As an example, the movement mechanism 220 may be in connection with a start button 105, as shown in FIG. 1A such that the movement mechanism 220 moves in the direction of the needle path 205 via the force applied when pushing the start button 105. Alternatively, as an example, a user may press the start button 105 which may cause one or more electronic components to generate and apply a force to the movement mechanism 220. It will be understood that one or more mechanical components such as pulleys, levers, or the like may be attached to the movement mechanism 220 to facilitate its movement.

As shown in FIGS. 2A-D, the movement mechanism 220 may create a portion of the needle path 205 such that a rigid needle 210 is placed in the movement mechanism 220. As shown in FIG. 2A, a first end 211 of the rigid needle 210 may be contained by a portion of the needle path 205 created by the movement mechanism 220.

According to an implementation, the movement mechanism 220 may contain a push surface 221 such that when movement mechanism 220 moves in the direction of the needle path 205, the first end 211 of the rigid needle 210 comes in contact with the push surface 221 of the movement mechanism 220. The push surface 221 may be composed of the same material or a different material as the rest of the movement mechanism 220. As the movement mechanism 220 moves in the direction of the needle path 205, the push surface 221 may apply a force on the first end 211 of the rigid needle 210. The applied force may push the rigid needle 210 to move along the needle path. As an example, as shown in FIG. 2A the movement mechanism 220 may be pushed in the horizontal direction 207. The push surface 221 may apply a force on the rigid needle 210 as a result of the movement. As a result of the force applied on the rigid needle 210, the rigid needle 210 may traverse along the needle path 205 such that the second end 212 of the rigid needle 210 moves in the vertical direction 208.

Alternatively, a first end 211 of the rigid needle 210 may be attached to the movement mechanism 220 via any applicable manner such as via a mechanical connection, an adhesive, or the like.

The movement mechanism 220 may move in the direction of the needle path 205 by gliding on components of the needle insertion mechanism 200. Alternatively, the movement mechanism 220 may be attached to rollers or wheels that allow the movement mechanism 220 to move in the direction of the needle path 205.

According to an implementation of the disclosed subject matter, the movement mechanism 220 may be configured to move a distance based on the force applied to the movement path. Alternatively, the movement mechanism 220 may be configured to move a predetermined distance such that, for example, the movement mechanism 220 is physically prevented from moving any further than the predetermined distance. Alternatively, or in addition, the movement mechanism 220 may provide feedback based on its position such that a user controlling the force applied to the movement mechanism is able to determine the degree to which the movement mechanism moves. The feedback may be, for example, increased resistance, a haptic response, or the like. Alternatively or in addition, one or more electronic components may be configured to move the movement mechanism 220 a distance corresponding to a specific use case or a user input.

Figure 2B:
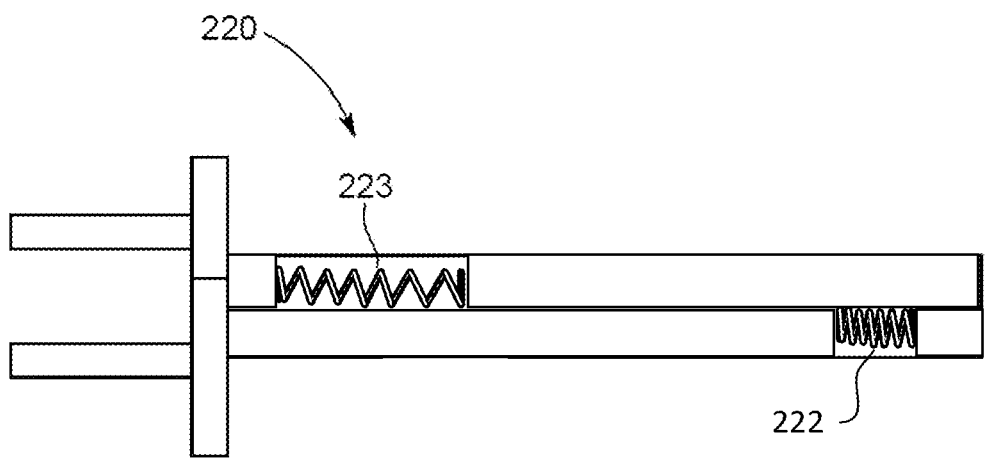
FIG. 2B is a graphical depiction of a needle insertion mechanism at a second position.

According to an implementation of the disclosed subject matter, an insertion spring 222, as shown in FIG. 2B may be compressed when the movement mechanism 220 moves from its first position to its second position. The insertion spring 222 may be compressed using the same force that is applied to move the movement mechanism 220 from its first position to its second position. Alternatively, the insertion spring 222 may be compressed independent of the force applied to move the movement mechanism 220 from its first position to its second position. According to an implementation of the disclosed subject matter, a retraction spring 223 may be expanded when the movement mechanism 220 moves from its first position to its second position. The retraction spring 223 may be expanded using the same force that is applied to move the movement mechanism 220 from its first position to its second position. Alternatively, the retraction spring 223 may be expanded independent of the force applied to move the movement mechanism 220 from its first position to its second position. It will be noted that the insertion spring 222 may initially produce a force that causes the movement mechanism 220 to move from its first position to its second position resulting in the cannula 240 being inserted into a users tissue. As a result of the movement, the retraction spring 223 may build up potential energy and produce a force in the opposite direction, such that the force in the opposite direction causes the movement mechanism 220 to move from its second position to its first position, causing the rigid needle 210 to traverse back along the needle path 205 away from the cannula 240, as further disclosed herein. To clarify, the insertion spring 222 may cause an initial movement of the movement mechanism 220 to move from a first position to a second position and the retraction spring 223 may cause a subsequent movement of the movement mechanism 220, to move from the second position to the first position. It will also be understood that although the forces generated by the insertion spring 222 and retraction spring 223 are disclosed independently, forces by each may be at least partially applied during the initial and subsequent movement.

Figure 2C:
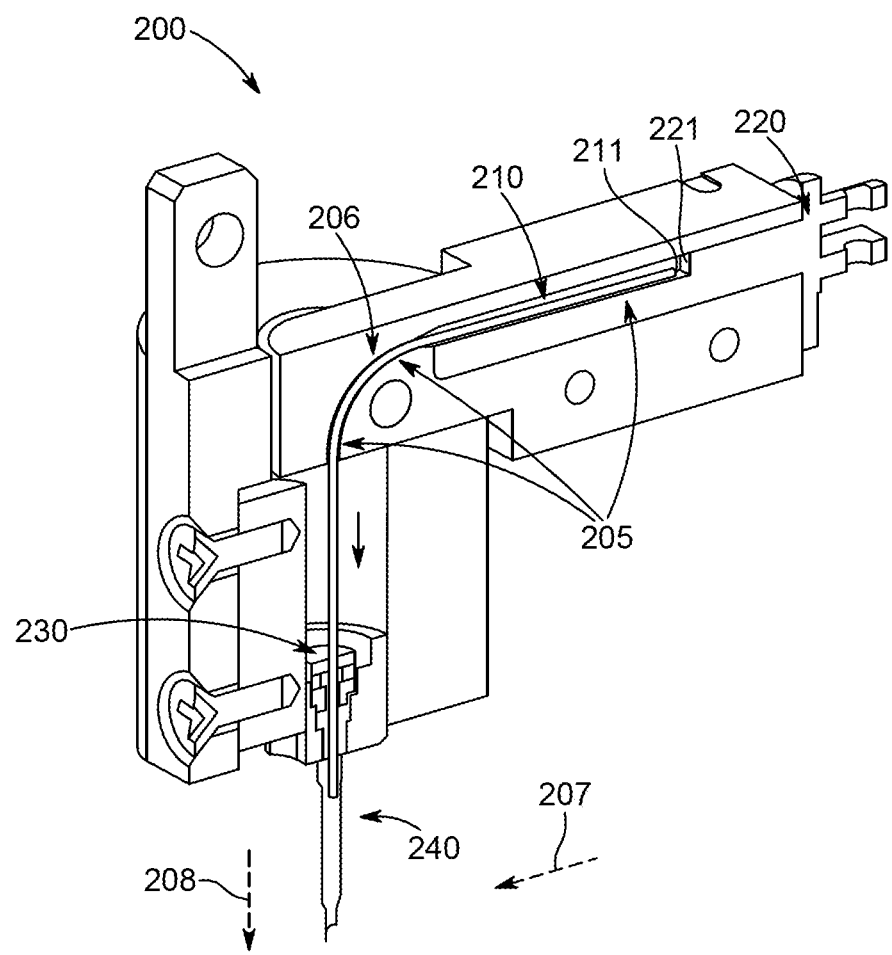
FIG. 2C is a graphical depiction of a needle insertion mechanism at a third position.

As shown in FIGS. 2A and 2C, the movement mechanism 220 may cause the rigid needle 210 to move from a first position shown in FIG. 2A to a second position shown in FIG. 2C. As disclosed above, the movement of the rigid needle 210 is caused by the movement mechanism 220 applying a force to the rigid needle 210, causing the rigid needle 210 to move from the first position to the second position. As shown in FIG. 2C, when the rigid needle 210 moves from the first position to the second position, a portion of the rigid needle 210 that may have been in a first location such as, for example, the substantially horizontal position in the direction 207 or on the curve 206 moves to a second location such as, for example, the substantially vertical position in the direction 208. Notably, the rigid needle 210 is configured to remain rigid while traversing through the needle path 205.

As shown in FIG. 2A, the cannula 240 is in a first position. As shown in FIG. 2C, the cannula 240 is moved from its first position to a second position. The cannula 240 is moved from the first position to the second position as a result of the rigid needle 210 moving from its first position to its second position and applying a force onto the cannula 240 as a result of its movement. The rigid needle 210 may apply a force on the cannula 240 by directly coming into contact with the cannula 240 such as, for example, by entering a first end of the cannula via an opening in the first end of the cannula. Alternatively, the first needle may come into contact with another component that is mechanically connected to the cannula 240 and is able to transfer the force applied by the rigid needle 210 to the cannula 240.

As shown in FIG. 2C, in moving to the second position, the cannula 240 may enter a users tissue 250. The cannula 240 may be connected to a fluid path that enables a solution, such as a drug, to be provided to the user via the cannula 240 when the cannula 240 is at its second position and inserted into the users tissue 250.

Figure 2D:
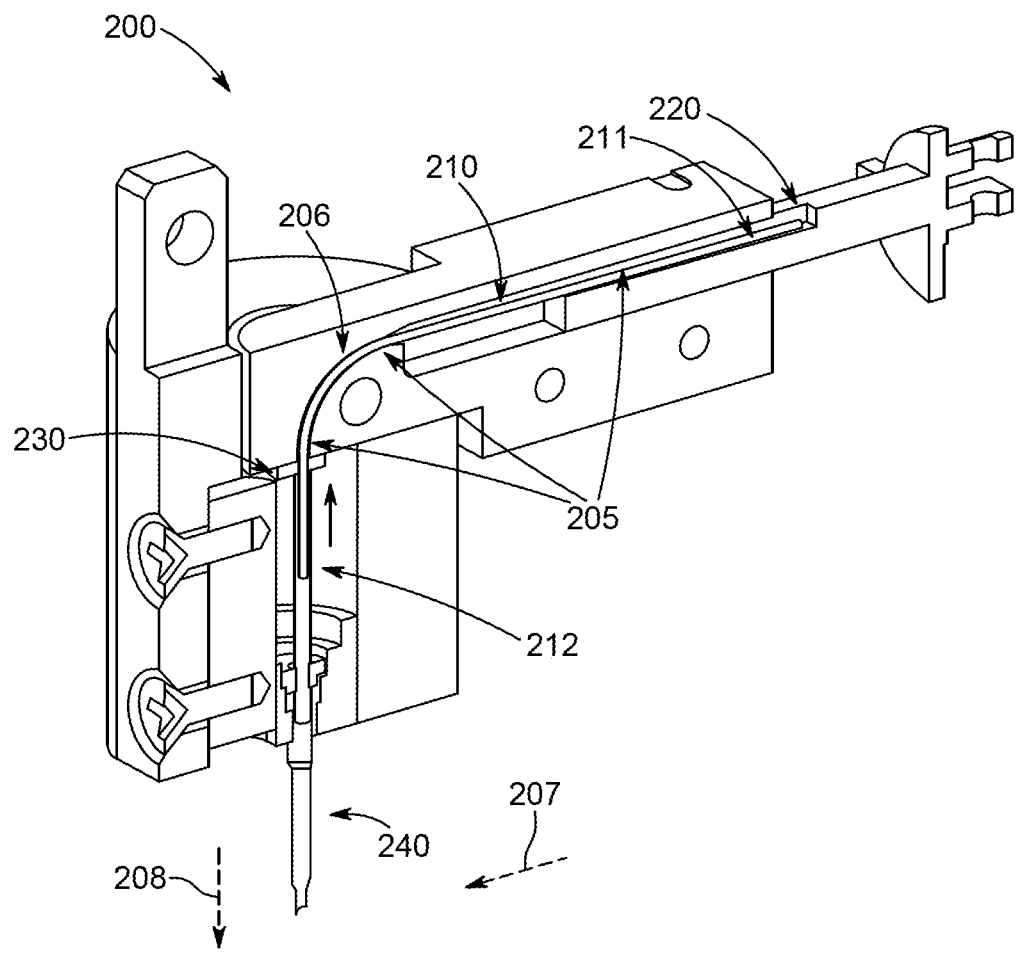
FIG. 2D is a graphical depiction of springs associated with the needle insertion mechanism.

FIG. 2D shows the needle insertion mechanism 200 where the movement mechanism 220 moves from its second position as shown in FIG. 2C, back to its first position. The movement mechanism 220 may move from its second position back to its first position as a result of the retraction spring 223 releasing from an expanded position to a compressed or neutral position. The insertion spring 222 may release from the expanded position to the compressed or neutral position as a result of potential energy stored in the expanded spring. Additionally, the rigid needle 210 may also move from its second position as shown in FIG. 2C, back to its first position.

As shown in FIG. 2D, the cannula 240 remains in its second position after the movement mechanism 220 and rigid needle 210 move from their respective second positions as shown in FIG. 2C, back to their respective first positions.

According to an implementation of the disclosed subject matter, a plate attachment 230, as shown in FIGS. 2A and 2C-D, may be affixed to the rigid needle 210. The plate attachment 230 may be affixed such that the plate attachment 230 is part of an end of the rigid needle 210 or may be attached to the rigid needle 210 via any applicable mechanical, adhesive, or other attaching technique. The plate attachment 230 may be configured to apply a force onto the cannula 240 to move the cannula 240 from its first position to its second position, as disclosed herein. The movement mechanism 220 may cause the plate attachment 230 to move from a first position shown in FIG. 2A to a second position shown in FIG. 2C. As disclosed above, the movement of the plate attachment 230 may be caused by the movement mechanism 220 applying a force to the rigid needle 210, causing the rigid needle 210 to move from the first position to the second position and, thus, causing the plate attachment 230 to move from its first position in FIG. 2A to its second position in FIG. 2C.

According to an implementation, as shown in FIG. 2D the plate attachment 230 moves with the rigid needle 210 and may retract from a second plate position to its first plate position when the rigid needle 210 moves from its second position back to its first position.

According to an implementation, the plate attachment 230 may detach from the rigid needle 210 and may remain at its second position after the rigid needle 210 moves from its second position back to its first position. According to this implementation, the plate attachment 230 may enable the cannula 240 to remain at its second position such that, for example, the cannula 240 remains within a user's tissue after the rigid needle 210 pulls back to its first position.

Figure 3:
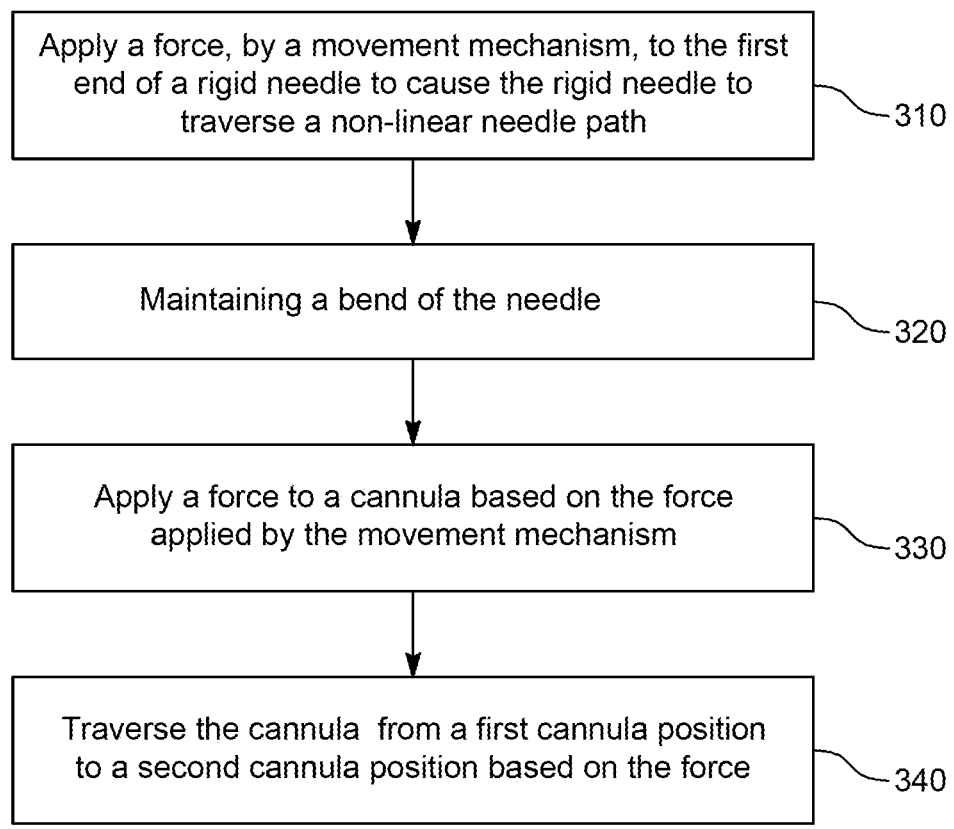
FIG. 3 is a flowchart for using a patch pump with needle insertion mechanism.

FIG. 3 shows an example flowchart for inserting a cannula into a user based on techniques disclosed herein. At 310, a movement mechanism may apply a force to a first end of a rigid needle to cause the rigid needle to traverse a non-linear path from a first needle position to a second needle position. At 320, the rigid needle may maintain a bend at a bend in the non-linear path such that the material that the rigid needle is composed of may allow for the needle to bend along the bend in the needle path. At 330, a force based on the force of the movement mechanism may be applied to a cannula such that, at 340, the cannula traverses from a first cannula position to a second cannula position based on the force.

Although features and elements are described above in particular combinations, one of ordinary skill in the art will appreciate that each feature or element can be used alone or in any combination with the other features and elements.

What is claimed is:

1. A device comprising:
a patch pump comprising a non-linear needle path, the non-linear needle path comprising a bend;
a rigid needle located in the non-linear needle path, the rigid needle having a length and a circular cross-section along the length and comprising a first material, wherein the first material enables the rigid needle to maintain a bend at the bend of the non-linear needle path when traversing the non-linear needle path;
a moveable member forming a portion of the non-linear needle path, the moveable member including a distal end, a push surface located proximal to the distal end, and a groove portion located between the distal end and the push surface, the groove portion arranged for containing the rigid needle therein, the moveable member configured to apply a first force on a first end of the rigid needle to cause the rigid needle to traverse the non-linear needle path from a first needle position to a second needle position, the moveable member being of one-piece construction, the push surface being integral with the moveable member and arranged to make direct contact with the first end of the rigid needle when the first force is applied; and
a cannula configured to receive a second force from a second end of the rigid needle when the moveable member applies the first force on the first end of the rigid needle and to traverse from a first cannula position to a second cannula position.

2. The device of claim 1, wherein the bend of the non-linear needle path configures the rigid needle to be at an angle of between 30 and 90 degrees between the first end of the rigid needle to the second end of the rigid needle.

3. The device of claim 1, wherein the cannula is further configured to enter a user's body due to the first force applied by the moveable member.

4. The device of claim 1, further comprising a retraction spring configured to retract the rigid needle from the second needle position to the first needle position.

5. The device of claim 4, wherein the cannula is configured to remain in the second cannula position when the rigid needle is retracted from the second needle position to the first needle position.

6. The device of claim 1, wherein the second end of the rigid needle comprises a plate attachment affixed at a first plate position.

7. The device of claim 6, wherein the plate attachment is configured to move to a second plate position when the rigid needle traverses from the first needle position to the second needle position.

8. The device of claim 7, wherein the plate attachment is configured to move from the second plate position to the first plate position when the rigid needle retracts from the second needle position to the first needle position.

9. The device of claim 7, wherein the plate attachment is configured to remain at the second plate position when the rigid needle retracts from the second needle position to the first needle position.

10. The device of claim 1, further comprising an insertion spring configured to extend from a first insertion spring position to a second insertion spring position to facilitate movement of the moveable member from a first moveable member position to a second moveable member position.

11. The device of claim 10, wherein the insertion spring is configured to compress from the second insertion spring position to the first insertion spring position as the moveable member moves from the second moveable member position to the first moveable member position.

12. The device of claim 1, further comprising a retraction spring configured to compress from a second retraction spring position to a first retraction spring position to facilitate movement of the moveable member from a second moveable member position to a first moveable member position.

13. The device of claim 12, wherein the retraction spring is configured to extend from the first retraction spring position to the second retraction spring position as the moveable member moves from the first moveable member position to the second moveable member position.

14. A method comprising:
   applying a first force by a moveable member to a first end of a rigid needle to cause the rigid needle to traverse a non-linear needle path from a first needle position to a second needle position, wherein the non-linear needle path comprises a bend, the rigid needle having a length and a circular cross-section along the length, the moveable member forming a portion of the non-linear needle path, the moveable member including a distal end, a push surface located proximal to the distal end, and a groove portion located between the distal end and the push surface, the groove portion arranged for containing the rigid needle therein, the moveable member being of one-piece construction, the push surface being integral with the moveable member and arranged to make direct contact with the first end of the rigid needle when the first force is applied;
   maintaining a bend of the rigid needle at the bend of the non-linear needle path while traversing the non-linear needle path from the first needle position to the second needle position, wherein the rigid needle comprises a material configured to enable the rigid needle to bend at the bend of the non-linear needle path;
   applying a second force to a cannula from a second end of the rigid needle when the moveable member applies the first force on the first end of the rigid needle; and
   traversing, by the cannula, from a first cannula position to a second cannula position based on the second force applied on the cannula from the second end of the rigid needle.

15. The method of claim 14, wherein the bend of the non-linear needle path configures the rigid needle to be at an angle of between 30 and 90 degrees between the first end of the rigid needle to the second end of the rigid needle.

16. The method of claim 14, further comprising the cannula entering a user's body due to the first force applied by the moveable member.

17. The method of claim 14, wherein the second end of the rigid needle comprises a plate attachment affixed at a first plate position.

18. The method of claim 17, further comprising moving the plate attachment from the first plate position to a second plate position when the rigid needle traverses from the first needle position to the second needle position.

19. The method of claim 14, further comprising retracting the rigid needle from the second needle position to the first needle position using a force generated by a retraction spring.

* * * * *